United States Patent
Xie

(10) Patent No.: US 10,424,738 B2
(45) Date of Patent: Sep. 24, 2019

(54) CONDENSED-CYCLIC COMPOUND, ELECTROLUMINESCENT DEVICE AND METHOD FOR MANUFACTURING THEREOF

(71) Applicant: Shenzhen China Star Optoelectronics Technology Co., Ltd., Shenzhen, Guangdong (CN)

(72) Inventor: Huafei Xie, Guangdong (CN)

(73) Assignee: Shenzhen China Star Optoelectronics Semiconductor Display Technology Co., Ltd, Shenzhen, Guangdong (CN)

( * ) Notice: Subject to any disclaimer, the term of this patent is extended or adjusted under 35 U.S.C. 154(b) by 220 days.

(21) Appl. No.: 15/536,085

(22) PCT Filed: May 12, 2017

(86) PCT No.: PCT/CN2017/084129
§ 371 (c)(1),
(2) Date: Jun. 14, 2017

(87) PCT Pub. No.: WO2018/192028
PCT Pub. Date: Oct. 25, 2018

(65) Prior Publication Data
US 2019/0088877 A1    Mar. 21, 2019

(30) Foreign Application Priority Data

Apr. 20, 2017   (CN) .......................... 2017 1 0262694

(51) Int. Cl.
*H01L 51/00* (2006.01)
*C09K 11/06* (2006.01)
(Continued)

(52) U.S. Cl.
CPC .......... *H01L 51/005* (2013.01); *C07C 47/546* (2013.01); *C09K 11/06* (2013.01);
(Continued)

(58) Field of Classification Search
None
See application file for complete search history.

(56) References Cited

U.S. PATENT DOCUMENTS

| 4,791,233 A | 12/1988 | Bair |
| 9,540,476 B2 | 1/2017 | Cui et al. |
| 2017/0101385 A1 | 4/2017 | Aker et al. |

FOREIGN PATENT DOCUMENTS

| CN | 1214337 A | 4/1999 |
| CN | 101200406 A | 6/2008 |

(Continued)

OTHER PUBLICATIONS

Shyi-Long Lee, et al. Theoretical studies of the molecular second-order hyperpolarizabilities of polycyclic aromatics, International Journal of Quantum Chemistry, 1995, pp. 518-519, vol. 56, No. 29.
(Continued)

*Primary Examiner* — Robert S Loewe
(74) *Attorney, Agent, or Firm* — Andrew C. Cheng

(57) ABSTRACT

A method for manufacturing a condensed-cyclic compound and an electroluminescent device is provided, the condensed-cyclic compound is represented by the following formula:

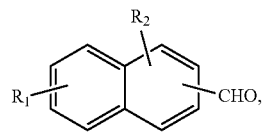

wherein —R1, —R2 and —CHO are connected to any one of an unsaturated carbon atom of a naphthalene ring; —R1, —R2 are respectively a hydrogen and any one of an alkane group or a condensed-cyclic aromatic hydrocarbon group.

(Continued)

The embodiments provided by the present invention using the above-described manner is able to reduce ACQ phenomenon of the condensed-cyclic compound in aggregate state or solid state.

9 Claims, 2 Drawing Sheets

(51) Int. Cl.
  *C07C 47/546* (2006.01)
  *H01L 51/50* (2006.01)
(52) U.S. Cl.
  CPC ...... *H01L 51/0052* (2013.01); *H01L 51/0054* (2013.01); *H01L 51/0055* (2013.01); *C07C 2603/24* (2017.05); *C09K 2211/1011* (2013.01); *H01L 51/001* (2013.01); *H01L 51/5012* (2013.01)

(56) References Cited

FOREIGN PATENT DOCUMENTS

| CN | 103194215 | A |   | 7/2013 |   |
|---|---|---|---|---|---|
| CN | 104311376 | A |   | 1/2015 |   |
| CN | 105601480 | A |   | 5/2016 |   |
| CN | 1911904 | A |   | 2/2017 |   |
| JP | 2007191441 | A | * | 8/2007 | ............... C07F 7/18 |
| JP | 2007224171 | A |   | 9/2007 |   |
| KR | 101545517 |   | * | 1/2006 | ............ C09K 11/06 |

OTHER PUBLICATIONS

Shen K.Yang, et al. Metabolism 8-hydroxymethylbenz[a] anthracene by rat liver microsomes stereochemistry of dihydrodiol metabolites and the effect of enzyme induction, Drug Metabolism and Disposition, 1984, pp. 405, vol. 12, No. 4.

Goverdhan Mehta, et al. A New Synthesis of Corannulene, Tetrahedron Letters, 1997, scheme 2, vol. 38, No. 12.

Youngmee Kim, et al. Synthesis of Oxidized Derivatives of 10-Deuterobenzo[A]Pyrene, Journal of the chinese Chemical Society, 1988, pp. 389, No. 5.

Robert E. Royer, et al. Synthesis of C-13 Labeled 6-Substituted Benzo(A)Pyrenes, Journal of Labelled compounds and radiopharmaceuticals,1976, pp. 378, vol. 12, No. 3.

Marta Glodek, et al. Direct Synthesis of Perylene-Fused Cyclic Ketones from Perylene and 2-Alkenoic Acids, European Journal of Organic Chemistry, 29, Jun. 2016, pp. 4218, scheme 6, vol. 2016, No. 24.

Kenneth W. Bair, et al. 2-[(Arylmethyl)amino]-2-methyl-I, 3-propanediol DNA Intercalators. An Examination of the Effects of Aromatic Ring Variation on Antitumor Activity and DNA Binding, J.Med.Chem. 1991, vol. 34, No. 7.

Animesh Sahana, et al. Cd(II)-triggered excimer-monomer conversion of a pyrenederivative: time dependent red-shift of monomer emission with cell staining application, Analyst, 2012, pp. 3910, sheme 1, vol. 137, No. 17.

Tianle Li, et al. Red electroluminescent devices based on rubrene derivative in 4,4'-N,N'-dicarubreneazole-biphenyl host and its application in white light emit ting device for lighting purpose, Solid-State Electronics, 03, Jan. 2009, pp. 120-121, vol. 53, No. 2.

* cited by examiner

ND-CYCLIC COMPOUND, ELECTROLUMINESCENT DEVICE AND METHOD FOR MANUFACTURING THEREOF

FIELD OF THE INVENTION

The present disclosure related to a field of organic electroluminescent device, especially related to a condensed-cyclic compound, an electroluminescent device and a method for manufacturing thereof.

BACKGROUND OF THE INVENTION

An organic electroluminescent device (OLED) has the advantages of simple structure, high yield, low cost, and active light emission, etc., thus becomes a hot topic in the field of flat panel display in recent years.

In an OLED preparation and optimization procedure, the choice of a luminescent material is essential; the property is one of the important factors determining the device performance. Currently, a condensed-cyclic compound is a classic fluorescent material, and also is one of the earliest luminescent materials found in an OLED device with an electroluminescent property and the most widely used.

The present inventors have found that in long-term studies, most of the condensed-cyclic compounds in the dissolved state have a strong fluorescence, while in aggregate state or solid state it has Aggregation-Caused Quenching (ACQ) phenomenon due to the non-radiative relaxation of the excited state of the aggregates. Also, in most industrial processes, ACQ effect is inevitable when a fluorescent material need to be prepared into aggregated, solid state, or thin film. Thus the application of such materials is greatly limited.

SUMMARY OF THE INVENTION

The objective of the present disclosure is to solve a technical problem of ACQ phenomenon of a condensed-cyclic compound in aggregate state or solid state by providing a condensed-cyclic compound, an electroluminescent device and a manufacturing method thereof.

To solve the above technical problem, an aspect of the present disclosure is: providing an electroluminescent device manufacturing method, which comprises: providing a substrate; disposing a hole transport layer on the substrate by spin coating or vapor deposition; disposing a light-emitting layer on the hole transport layer by vapor depositing, wherein a material of the light-emitting layer is a condensed-cyclic compound, the condensed-cyclic compound is represented by a following general formula:

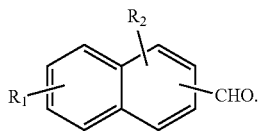

Wherein —R1, —R2 and —CHO are connected to any one of an unsaturated carbon atom of a naphthalene ring; —R1, —R2 are respectively a hydrogen and any one of an alkane group or a condensed-cyclic aromatic hydrocarbon group, the alkane group is —CnH2n+1, where 1≤n≤12; the condensed-cyclic aromatic hydrocarbon group is a benzene, a naphthalene, an anthracene, a pyrene, a phenanthrene or a perylene group; and vapor depositing an electron transport layer and a metal cathode layer on the light-emitting layer sequentially.

To solve the above technical problem, an aspect of the present disclosure is: providing a condensed-cyclic compound; the condensed-cyclic compound is represented by the following general formula:

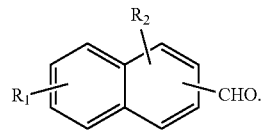

Wherein —R1, —R2 and —CHO are connected to any one of an unsaturated carbon atom of a naphthalene ring; —R1, —R2 are respectively a hydrogen and any one of an alkane group or a condensed-cyclic aromatic hydrocarbon group.

To solve the above technical problem, another aspect of the present disclosure is: providing an electroluminescent device, the electroluminescent device comprises a light-emitting layer, wherein the light-emitting layer comprises a condensed-cyclic compound of the above embodiment.

The beneficial effects of the present disclosure are: apart from the current technologies, the present disclosure provides a condensed-cyclic compound, which is represented by the following general formula:

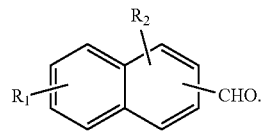

An aldehyde group introduced on the condensed-cyclic compo and makes the original conjugated planar configuration into a stereoscopic configuration, the aldehyde group is linked to the conjugate center of the condensed-cyclic compound via a rotatable single bond. While in aggregate or solid state, an internal rotation of the molecule is blocked, a non-radiative relaxation channel is suppressed, an excited state molecule can only return to ground state by radiation decay due to the presence of the aldehyde. Therefore, reducing the ACQ phenomenon of a condensed-cyclic compound in aggregate state or solid state, and increasing the application of the condensed-cyclic compound.

DETAILED DESCRIPTION OF PREFERRED EMBODIMENTS

Figure 1:
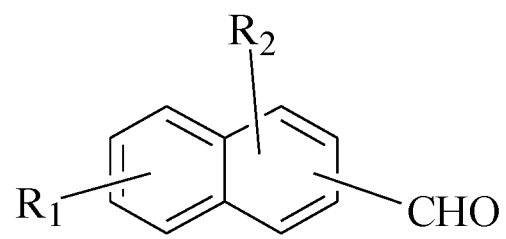
FIG. 1 is a schematic structure diagram showing an embodiment of a condensed-cyclic compound of the present disclosure.

Referring to FIG. 1, FIG. 1 is a schematic structure diagram showing an embodiment of a condensed-cyclic compound in the present disclosure. The condensed-cyclic compound is represented by a following general formula:

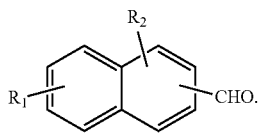

Wherein —R1, —R2 and —CHO are connected to any one of an unsaturated carbon atom of a naphthalene ring; —R1, —R2 are respectively a hydrogen and any one of an alkane group or a condensed-cyclic aromatic hydrocarbon group; when —R1, —R2 is a hydrogen or an alkane group, it can be connected to an unsaturated carbon atom at any position of a naphthalene ring; when —R1, —R2 is a condensed-cyclic aromatic hydrocarbon group, it can be connected to at least two unsaturated carbon atoms adjacent to the naphthalene ring, the present disclosure is not limited thereto. In one embodiment, the above alkane group is —$C_nH_{2n+1}$, where 1≤n≤12; for example, —$CH_3$, —$C_5H_{11}$, and —$C_{12}H_{25}$ and so on. Further, the alkane group can be a straight chain alkane group or a branched alkane group as well. In another embodiment, the above condensed-cyclic aromatic hydrocarbon group is a benzene, a naphthalene, an anthracene, a pyrene, a phenanthrene or a perylene group.

When the condensed-cyclic aromatic hydrocarbon group is a benzene, the structure of the condensed-cyclic compound can be:

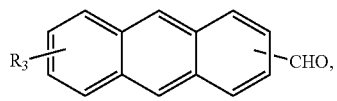

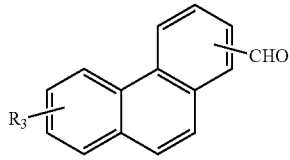

and so on.

When the condensed-cyclic aromatic hydrocarbon group is a naphthalene, the structure of the condensed-cyclic compound can be:

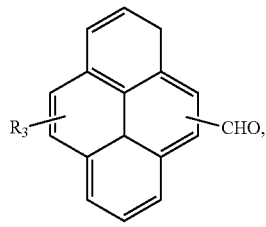

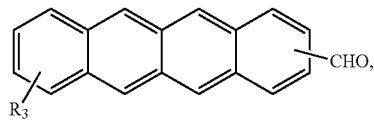

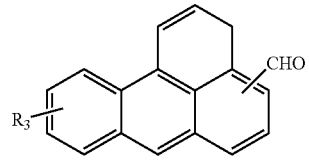

and so on.

When the condensed-cyclic aromatic hydrocarbon group is an anthracene, the structure of the condensed-cyclic compound can be:

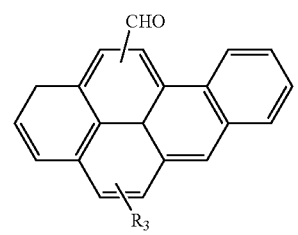

and like.

When the condensed-cyclic aromatic hydrocarbon group is a pyrene, the structure of the condensed-cyclic compound can be:

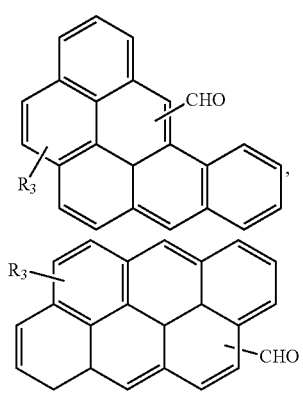

and so on.

When the condensed-cyclic aromatic hydrocarbon group is a phenanthrene, the structure of the condensed-cyclic compound can be:

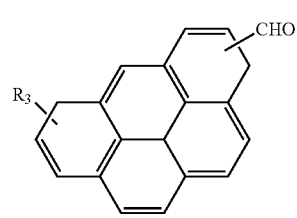

and like.

When the condensed-cyclic aromatic hydrocarbon group is a phenanthrene, the structure of the condensed-cyclic compound can be:

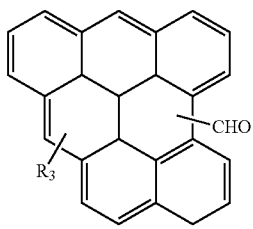

and like.

Of course, the structure of the condensed-cyclic compound of the present disclosure is not limited to the above examples, the design can be selected according to the actual situation. Further, the above —R3, —CHO are connected on any one of the unsaturated carbon atom, —R3 is a hydrogen or an alkane group, the alkane group is —$C_nH_{2n+1}$, where $1 \leq n \leq 12$, for example —$CH_3$, —$C_5H_{11}$, and —$C_{12}H_{25}$, and so on. The above alkane group can be a straight chain alkane group or a branched alkane group.

To prepare the above condensed-cyclic compound, in one embodiment, it can be prepared by using the Vilsmeier-Haack reaction, the chemical reaction equation is as follows:

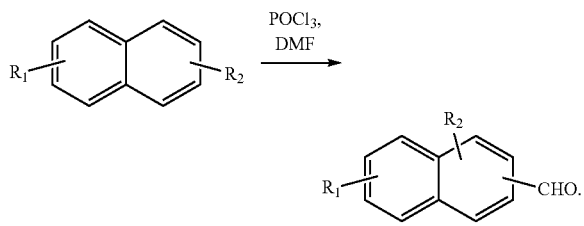

Specifically, by using phosphorus oxychloride (POCl3) and dimethylformamide(DMF) as vilsmiere reagent, the above reaction is carried out by microwave or heating, and then —CHO is introduced into the naphthalene ring of the above reactants.

A condensed-cyclic compound with an aldehyde group introduction as described above has an effect of aggregation-induced luminescence, this is because

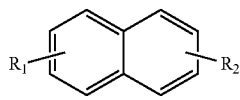

has a conjugated planar configuration in aggregate state or solid state. The π-π interaction between molecules or other non-radiative channel forms an excimer or an exciplex, and then consumes excitation energy, thereby reduces fluorescence or even no fluorescence emission. When a naphthalene ring is introduced into an aldehyde group and forming

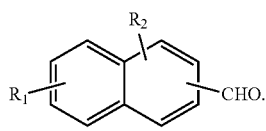

The molecular structure becomes a stereoscopic configuration, an aldehyde group and a conjugate center are connected via a rotatable single bond. When in aggregate state or solid state, due to space constraints, intramolecular rotation is limited, a non-radiative decay channel is suppressed, an excited state molecule can return to ground state by radiation decay, so that the fluorescence is significantly enhanced. That is, a condensed-cyclic compound has an effect of aggregation-induced luminescence, therefore it reduces the ACQ phenomenon of a condensed-cyclic compound in aggregate state or solid state, which broadens its field of application.

In one application, since a condensed-cyclic compound has an effect of aggregation-induced luminescence, the condensed-cyclic compound can be applied as a luminescent material, for example, it can be used as an optical organic thin film, an electroluminescent device and so on.

The following case as an example of an electroluminescent device, the condensed-cyclic compound is further described on the application of a luminescent material.

Figure 2:
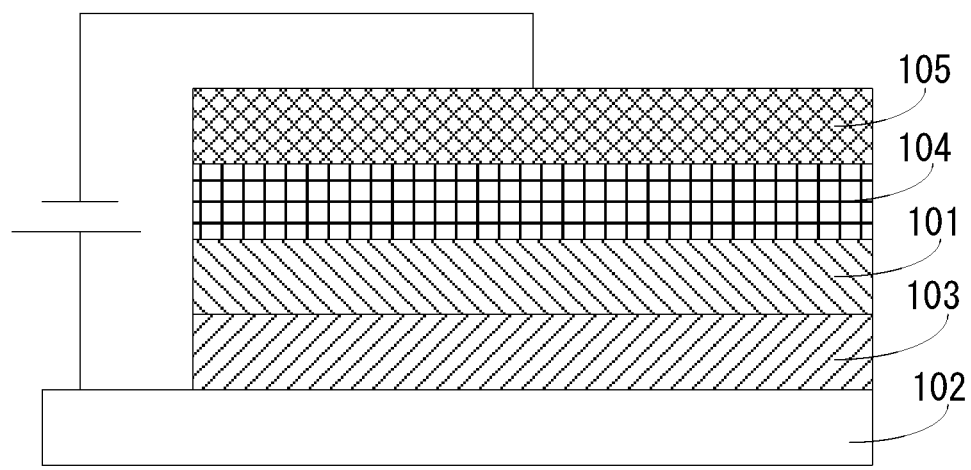
FIG. 2 is a schematic structure diagram showing an embodiment of an electroluminescent device of the present disclosure.

Referring to FIG. 2, FIG. 2 is a schematic structure diagram showing an embodiment of an electroluminescent device in the present disclosure, the electroluminescent device comprises a light-emitting layer 101, a material of the light-emitting layer is a condensed-cyclic compound in any one of the above embodiments, it will not be repeated herein. In other embodiments, the above electroluminescent device further comprises:

A substrate 102 disposed on a side of the light-emitting layer 101 is serving as an anode of the device. In one application, the work function of the substrate 102 material is high, it can be ITO (indium tin oxide).

A hole transport layer 103 disposed between the substrate 102 and the light-emitting layer 101, is functioned to enhance the transport of a hole in the device, and preferably offers a blocking effect on an electronic. The material is PEDOT:PSS (Poly (3,4-ethylenedioxythiophene):polystyrene sulfonate), NPB (N,N'-bis(1-naphthyl)-N, N'-diphenyl-1,1'-biphenyl-4-4'-diamine), etc.

An electron transport layer 104 disposed on another side of the light-emitting layer 101 opposite to the substrate 102, is functioned to transport an electron, preferably offers a blocking effect on a hole, so that the electron can be efficiently into the light-emitting layer. The materials can be TPBi (1,3,5-tris(1-phenyl-1H-benzimidazol-2-yl) benzene) and Alq3 (8-hydroxyquinoline aluminum).

A metal cathode layer 105 is disposed on a surface of the electron transport layer 104 opposite to the light-emitting layer 101, the work function of which is generally low, and the material can be LiF (lithium fluoride)/Al (aluminum), Mg (magnesium), Ag (silver), etc.

In one embodiment, in order to prepare the electroluminescent device of the above structure, the following steps may be adopted: washing the substrate 102; disposing the hole transport layer 103 on the substrate 102 by spin coating or vapor deposition; disposing the electron transport layer 104 and the metal cathode layer 105 on the light-emitting layer 101 by vapor deposition sequentially.

The structure of the electroluminescent device in the above embodiment is a multilayer structure, other structures can also be used in other embodiments, as long as it comprises a light-emitting layer, and the luminescent layer material is a condensed-cyclic compound in the above embodiments; the manufacturing method can also be changed according to the actual situation.

The following will briefly introduce a light-emitting process of the electroluminescent device, comprising the steps of: A. injecting a carrier: an electron and a hole are respectively injected into the device to from a cathode (the metal cathode layer 105) and an anode (the substrate 102) of the device; B. transporting the carrier: the electron and the hole migrate respectively from the electron transport layer 104 and the hole transport layer 103 to the light-emitting layer 101; C. recombining the carrier to form an exciton: the electron and the hole meet in the light emitting layer 101 and recombine into an exciton. D. diffusing the exciton: exciton diffusion transfers energy to a condensed-cyclic compound of the luminescent layer 101, and making an electron in the condensed-cyclic compound to be excited from ground state to excited state; E. retreating an exciting light: excited state is an unstable state, the electron in excited state of the condensed-cyclic compound returns to ground state, and energy released in the form of a photon, and then the electroluminescent device starts to emit light. In one application, a brightness of the electroluminescent device is 1000 cd/m² to 6000 cd/m², with an external quantum efficiency is 1% to 3%, under a current density of 0.5 A/cm² to A/cm².

The present disclosure will be further explained by the following specific embodiments.

Embodiment 1: Preparing a Condensed-Cyclic Compound 9-anthracene aldehyde

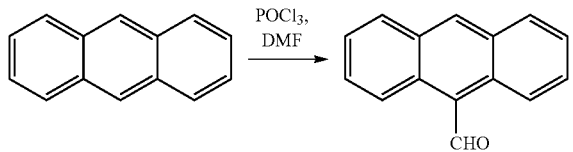

Figure 3:
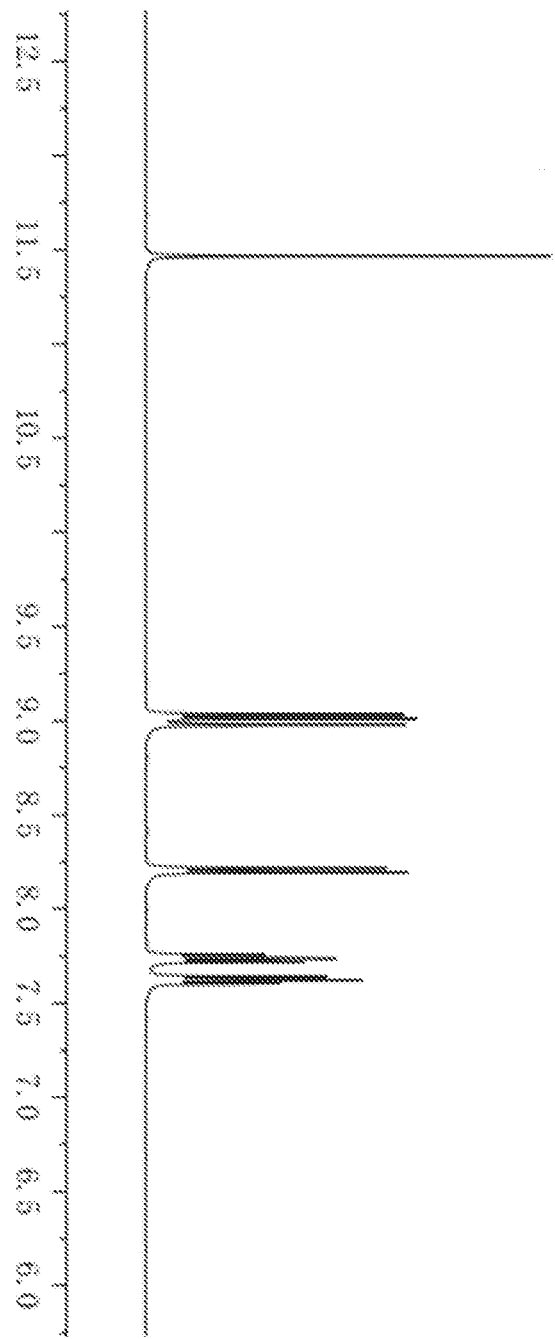
FIG. 3 is a schematic characterization diagram of an embodiment showing a nuclear magnetic resonance of 9-anthracene aldehyde.

Mixing 55 g of POCl3 and 30 g of anthracene and heating to 90° C.-95° C., dropping 19 g of DMF slowly, reaction 15 h to get the product 9-anthracene aldehyde; FIG. 3 is a schematic characterization diagram showing a nuclear magnetic resonance of 9-anthracene aldehyde embodiment.

Embodiment 2: Characterization of the Fluorescence Quantum Yield of 9-anthracene aldehyde As shown in the following table 1, when the solvent is DMSO (dimethyl sulfoxide), 9-anthracene aldehyde has a high solubility in DMSO, an aldehyde group in 9-anthracene aldehyde free rotates around a single bond, consumes excitation state energy, and becomes non-radiative decay. So that 9-anthracene aldehyde has almost no fluorescence and the quantum yield is almost zero. When 9-anthracene aldehyde is dispersed in the mixture of DMSO:H2O=1:99, due to the solubility of 9-anthracene aldehyde in water is low, 9-anthracene aldehyde is in agglomerate state in the mixture and emits yellow fluorescence, the quantum yield is 14.2%, thus confirming that the condensed-cyclic compound of the present disclosure is an aggregation-induced emission compound.

TABLE 1 fluorescence quantum yield of 9-anthracene aldehyde.

| condensed-cyclic compound | solvent | fluorescence maximum excitation wavelength (nm) | fluorescence maximum emission wavelength (nm) | fluorescence quantum yield, % |
|---|---|---|---|---|
| 9-anthracene aldehyde | DMSO | 365 | — | ~0 |
| 9-anthracene aldehyde | DMSO:H2O = 1:99 | 365 | 516 | 0.142 |

Embodiment 3: Preparing the Electroluminescent Device by 9-Anthracene Aldehyde and Characterizing its Performance Under high vacuum conditions, a hole transport layer NPB (60 nm) is deposited on the cleaned conductive ITO substrate, and then disposing the light emitting layer 9-anthracene aldehyde, the electron transport layer TPBI (20 nm)/Alq3 (30 nm) and the metal cathode layer LiF (1 nm)/Al (100 nm) by vapor deposition sequentially.

After testing, the electroluminescent device has a yellow emission peak at 520 nm, and luminance of the device up to 3500 cd/m², power is 27 m/W, external quantum efficiency is 2.2% under a current density of 3 A/cm².

In summary, apart from the current technologies, the present disclosure provides a condensed-cyclic compound, the condensed-cyclic compound is represented by the following general formula:

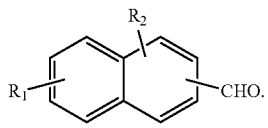

An aldehyde group introduced on the condensed-cyclic compound makes the original conjugated planar configuration into a stereoscopic configuration, the aldehyde group is linked to the conjugate center of the condensed-cyclic compound by a rotatable single bond. While in aggregate or solid state, an internal rotation of the molecule is blocked, a non-radiative relaxation channel is suppressed, an excited state molecule can only return to ground state by radiation decay due to the presence of the aldehyde. Therefore, reducing the ACQ phenomenon of a condensed-cyclic compound in aggregate state or solid state, and increasing the application of the condensed-cyclic compound.

The embodiments described above are only embodiments of the present disclosure, not intended to limit the scope of the present disclosure, all utilize the present specification and drawings taken equivalent structures or equivalent process, or other direct or indirect application related technical fields shall fall within the scope of protection of the present disclosure.

What is claimed is:

1. A method of manufacturing an electroluminescent device, comprising the steps of:
providing a substrate;
spin coating or vapor depositing a hole transport layer on the substrate;
vapor depositing a light-emitting layer on the hole transport layer, wherein a material of the light-emitting layer is a condensed-cyclic compound, the condensed-cyclic compound is represented by a following general formula:

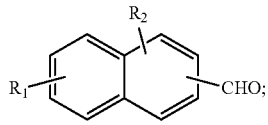

wherein —R1, —R2 and —CHO are connected to any one of an unsaturated carbon atom of a naphthalene ring; —R1, —R2 are respectively a hydrogen and any one of an alkane group or a condensed-cyclic aromatic hydrocarbon group, the alkane group is —CnH2n+1, where 1≤n≤12;

the condensed-cyclic aromatic hydrocarbon group is a benzene, a naphthalene, an anthracene, a pyrene, a phenanthrene or a perylene group; and vapor depositing an electron transport layer and a metal cathode layer on the light-emitting layer sequentially.

2. The method of manufacturing an electroluminescent device according to claim 1,
wherein the condensed-cyclic compound is selected from any one of the following compounds:

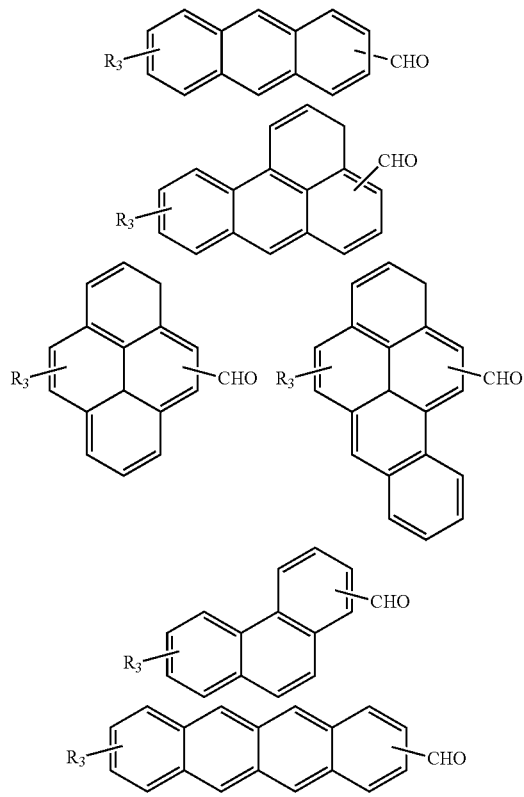

wherein —R3, —CHO are connected on any one of the unsaturated carbon atom, —R3 is a hydrogen or an alkane group, the alkane group is —CnH2n+1, where 1≤n≤12.

3. The method of manufacturing an electroluminescent device according to claim 1, wherein the condensed-cyclic compound is derived from a corresponding reactant

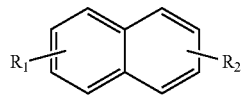

via Vilsmeier-Haack reaction.

4. An electroluminescent device comprising a light-emitting layer, wherein the light-emitting layer comprises a condensed-cyclic compound; the condensed-cyclic compound is represented by the following general formula:

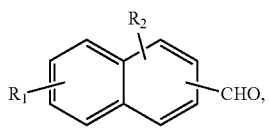

wherein —R1, —R2 and —CHO are connected to any one of an unsaturated carbon atom of a naphthalene ring; —R1, —R2 are respectively a hydrogen and any one of an alkane group or a condensed-cyclic aromatic hydrocarbon group.

5. The electroluminescent device according to claim 4, wherein the alkane group is —CnH2n+1, where 1≤n≤12, the condensed-cyclic aromatic hydrocarbon group is a benzene, a naphthalene, an anthracene, a pyrene, a phenanthrene or a perylene groups.

6. The electroluminescent device according to claim 5, wherein the condensed-cyclic compound is selected from any one of the following compounds:

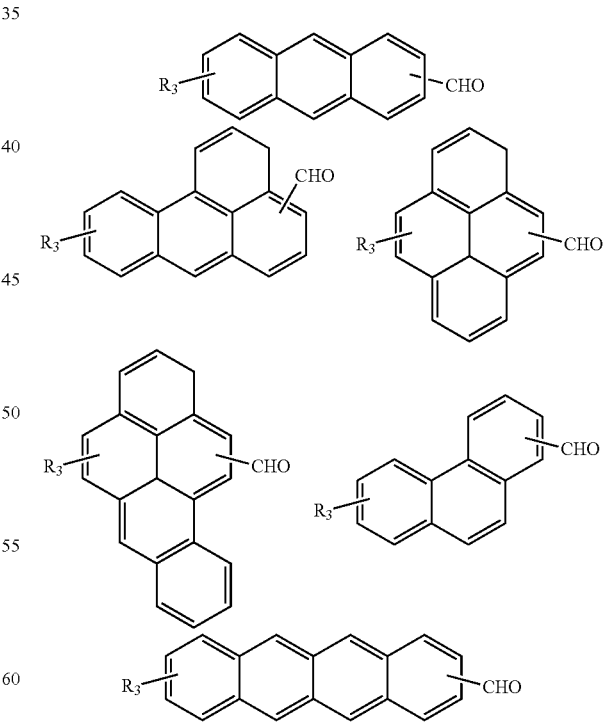

wherein —R3, —CHO are connected to any one of the unsaturated carbon atoms, —R3 is a hydrogen or an alkane group, the alkane group is —CnH2n+1, where 1≤n≤12.

7. The electroluminescent device according to claim 4, wherein the condensed-cyclic compound is derived from a corresponding reactant

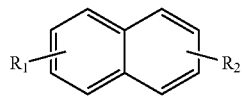

via Vilsmeier-Haack reaction.

8. The electroluminescent device according to claim 4, wherein the device further comprises:
- a substrate disposed on a side of the light-emitting layer, serving as an anode of the device;
- a hole transport layer disposed between the substrate and the light-emitting layer;
- an electron transport layer disposed on another side of the light-emitting layer opposite to the substrate;
- a metal cathode layer disposed on a surface of the electron transport layer opposite to the light-emitting layer.

9. The electroluminescent device according to claim 4, wherein a brightness of the electroluminescent device is 1000 cd/m$^2$ to 6000 cd/m$^2$, with an external quantum efficiency is 1% to 3%, under a current density of 0.5 A/cm$^2$ to 5 A/cm$^2$.

* * * * *